United States Patent
Smirnov et al.

(10) Patent No.: US 8,044,210 B2
(45) Date of Patent: Oct. 25, 2011

(54) SUBSTANCE HAVING ANTIOXIDANT, GEROPROTECTIVE AND ANTI-ISCHEMIC ACTIVITY AND METHOD FOR THE PREPARATION THEREOF

(75) Inventors: Leonid Dmitrievich Smirnov, Moscow (RU); Larisa Kasimirovna Smirnova, legal representative, Moscow (RU); Michail Arkadievich Ostrovsky, Moscow (RU); Aleksey Michailovich Sipyagin, Moscovskaya (RU); Natalia Y. Sipyagina, legal representative, Moscovskaya (RU); Nadezda A. Sipyagina, legal representative, Moscovskaya (RU); Aleksandr Evgenievich Doncov, Moscow (RU)

(73) Assignee: Marvel Lifesciences Limited, London (GB)

( * ) Notice: Subject to any disclaimer, the term of this patent is extended or adjusted under 35 U.S.C. 154(b) by 0 days.

(21) Appl. No.: 12/338,342

(22) Filed: Dec. 18, 2008

(65) Prior Publication Data

US 2009/0198068 A1    Aug. 6, 2009

Related U.S. Application Data

(63) Continuation of application No. 11/995,285, filed as application No. PCT/IB2005/003636 on Nov. 7, 2005, now abandoned.

(51) Int. Cl.
C07D 211/72 (2006.01)
A61K 31/435 (2006.01)

(52) U.S. Cl. .................. 546/290; 514/277

(58) Field of Classification Search .............. 546/290; 514/277

See application file for complete search history.

(56) References Cited

FOREIGN PATENT DOCUMENTS

| RU | 2070010 C1 | 12/1996 |
| RU | 2112512 C1 | 6/1998 |
| RU | 2153872 C2 | 8/2000 |
| RU | 2004114314 C2 | 5/2006 |

OTHER PUBLICATIONS

Physical Characterization of Pharmaceutical Solids, 1995, V. 70, p. 344.*
Brittain, H. G., Physical Characterization of Pharmaceutical Solids, Drugs and the Pharmaceutical Sciences, vol. 70, p. 344, 1995.*
Hcaplus 1970:486385 Abstract, "Kinetic characteristics of synthetic inhibitors and their relation to antitumoral action", Khrapova, N. G., 1970.*
Wijtmans, J. Org. Chem. 2004, vol. 69, pp. 9215-9223.*
M.D. Mashkovsky, "Pharmaceuticals", part II, 1993, Moscow, Medicine, p. 216.

* cited by examiner

Primary Examiner — Janet Andres
Assistant Examiner — Heidi Reese
(74) Attorney, Agent, or Firm — Robert P. Michal; Lucas & Mercanti, LLP

(57) ABSTRACT

The invention relates to the field of medicine, namely to new biologically active compounds, particularly to 2,4,6-trimethyl-3-hydroxypyridine derivatives and salts thereof (compound 1) having antioxidant, geroprotective and anti-ischemic action. The salts of compound (1) are prepared by reacting equimolecular quantities of 2,4,6-trimethyl-3-hydroxypyridine and dicarboxylic in solution of a lower alcohol at a temperature of 60-100° C. with following treatment of the reaction mass with an organic solvent and maintaining for 2-5 h at 10-15 ° C.

1 Claim, No Drawings

SUBSTANCE HAVING ANTIOXIDANT, GEROPROTECTIVE AND ANTI-ISCHEMIC ACTIVITY AND METHOD FOR THE PREPARATION THEREOF

This application is a continuation of Ser. No. 11/995,285, which is a National Phase entry of PCT/IB2005/003636 filed Jul. 11, 2005.

The invention relates to the field of medicine, namely to new biologically active compounds, and specifically to 2,4,6-trimethyl-3-hydroxypyridine salts with lower dicarboxylic acids (compound Ia-d), having antioxidant, geroprotective and anti-ischemic activity. Compounds Ia-d show antioxidant activity regarding the process of peroxide oxidation of lipids, that is appropriate to all 3-oxypyridine derivatives. This property allows to assume, that compounds Ia-d, as well as their analogs emoxypine (hydrochloride 2-methyl-6-ethyl-3-hydroxypyridine) and mexydole (2-methyl-6-ethyl-3-hydroxypyridine succinate), can be used as medical agents in opthalmology, namely, at subconjunctival and ocular hemorrhages into any parts and tissues of the eye, angioretinopathies of different etiologies, including diabetic, chorioretinal dystrophies, retinal central vein thrombosis and vein branches, complicated myopia, dystrophy keratites, and for protection and treatment of cornea and retina under the influence of light of high effectiveness after operations with retinal detachment. Furthermore, compound Ic having expressed anti-ischemic activity is assumed to be possibly used in cardiology for treating ischemic heart disease and atherosclerosis.

Compound Ic has also been found to be an active inhibitor of photoinduced peroxide oxidation of lipids sensitized by "senile pigment" being lipofuscin granules, isolated from eyes of elderly people indicating that compound Ic is capable of neutralizing toxic activity of lipofuscin granules accumulated in senior age, i.e. to have geroprotective action. Thus, it is possible to assume, that compound Ic may be used to inactivate the toxic action of lipofuscin. The lipofuscin, as now commonly accepted, is a basic factor leading to development of senile macular retinal degeneration. The senile macular retinal degeneration belongs to the most widespread ophthalmic diseases of people above the age of 60 years. According to statistical data said disease leading to full blindness, affects almost 30% of the Americans at the age of above 65 years, and the percentage of diseased people fast increases with the age.

A medicine for antioxidant protection of media and tissues of the eye being a biosolvable polymer with a hydrophylic plasticizing additive, and comprising emoxypine and piroxydine hydrochloride as a drug is known (RU 2070010, 1993).

The bioactive food additive "glutapiron" having inter alia geroprotective activity, and comprising salts of 2-(2,6-dimethyl-3,5-dietoxycarbonile-1,4-dihydropyridine-4-carboxamido)pentane diacid as active agent is known (RU 95116403, 1995).

The use of dipotassic salt of N-(3-chloro-1,4-naphtohynonyl)-2-glutamic acid as an agent showing inter alia anti-ischemic activity is also known.

Closest prior art with respect to the present invention represents 2-methyl-6-ethyl-3-hydroxypyridine succinate (mexydole) (M. D. Mashkovsky, "Pharmaceuticals", part II, 1993, Moscow, Medicine, page 216), having antioxidant and membranoprotective action, said substance being prepared by heating of an alcoholic solution of 2-methyl-6-ethyl-3-hydroxypyridine with succinic acid for 1 hour (SU 509047, 1973).

It is an object of the present invention to provide new substances being derivatives of 3-hydroxypyridine family having antioxidant, geroprotective and anti-ischemic properties that do not show an irritant effect on the tissue of the eye.

The essence of the present invention consists in new compounds representing pharmaceutically acceptable 2,4,6-trimethyl-3-hydroxypyridine salts with lower dicarboxylic acids of the general formula Ia-d having antioxidant, geroprotective and anti-ischemic activities:

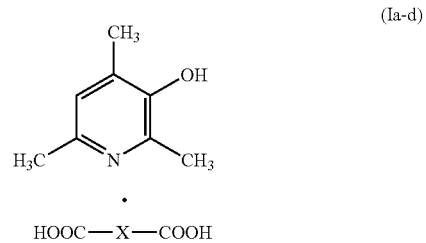

(Ia-d)

with X being a simple bond (compound Ia, oxalate, $C_8H_{11}NO.C_2H_2O_4$);
with X being $CH_2$ (compound Ib, malonate, $C_8H_{11}NO.C_3H_4O_4$);
with X being $CH_2CH_2$ (compound Ic, succinate, $C_8H_{11}NO.C_4H_6O_4$);
with X being the group $CH_2CH(OH)$ (compound Id, malate, $C_8H_{11}NO.C_4H_6O_5$).

It is another object of the present invention to provide a method for preparing 2,4,6-trimethyl-3-hydroxypyridine salts having antioxidant, geroprotective and anti-ischemic activities, the method comprising reacting equimolecular quantities of 2,4,6-trimethyl-3-hydroxypyridine and dicarboxylic acid in solution of a lower alcohol at a temperature of 60-100° C. and following treatment of the reaction mass with an organic solvent, and maintaining for 2-5 hours at 10-15° C.

EXAMPLE 1

Preparation of Organic Salts of 2,4,6-trimethyl-3-oxypyridine

A). Preparation of 2,4,6-trimethyl-3-oxypyridine oxalate (Ia)

0.8 g (0.00583 mol) 2,4,6-trimethyl-3-oxypyridine base, 0.525 g (0.00583 mol) waterless oxalic acid and 10 ml of methanol are fed to a flask with a magnetic stirrer and reflux condenser. Under stirring the reaction mixture is heated to boiling and kept boiling for 0.5 hours. Subsequently, the heating is stopped, the solvent is stripped off in vacuum, and 5 ml of acetone are added to the reaction mixture, and the mixture is triturated with a glass rod for 5-10 min. The resulting crystalline residue is separated by filtrating and is washed on the filter with acetone, and is dried in vacuum.

1.1 g (83% of the theory) of the salt are obtained. The melting temperature is 140-142° C. Obtained, %: C, 53.4, H 5.9. Calculated, %: C, 52.9, H 5.8.

NMR-$^1$H Bruker WM-400 (400 MHz) (DMSO-$d_6$): 2,20 (3H, s, $CH_3$); 2,34 (3H, s, $CH_3$); 2,37 (3H, s, $CH_3$); 7,05 ppm (1H, s, CH).

B). Preparation of 2,4,6-trimethyl-3-oxypyridine malonate (Ib)

0.8 g (0.00583 mol) 2,4,6-trimethyl-3-oxypyridine base, 0.607 g (0.00583 mol) malonic acid and 10 ml ethanol are fed to a flask with a magnetic stirrer and reflux condenser. Under stirring the reaction mixture is heated to boiling and kept boiling for 0.5 hours. Subsequently, the heating is stopped, the solvent is stripped off in vacuum, and 5 ml of acetone are added to the reaction mixture, the mixture being maintained for 3 hours at 10-15° C. The resulting crystalline residue is triturated, separated by filtrating, and is washed on the filter with acetone and dried in vacuum. 1.2 g (85.3% from the theory) of the salt are obtained. The melting temperature is 118-120° C. Obtained, %: C, 55.0, H 6.5. Calculated, %: C, 54.8, H 6.3.

NMR-$^1$H Bruker WM-400 (400 MHz) (DMSO-$d_6$): 2,16 (3H, s, $CH_3$); 2,30 (3H, s, $CH_3$); 2,33 (3H, s, $CH_3$); 3,11 (2H, s, $CH_2$); 6,93 ppm (1H, s, CH).

C). Preparation of 2,4,6-trimethyl-3-oxypyridine succinate (Ic)

3.4 g (0.025 mol) of 2,4,6-trimethyl-3-oxypyridine base, 2.93 g of (0.025 mol) succinic acid and 50 ml of izopropanol are fed to a flask with a magnetic stirrer and reflux condenser. Under stirring the reaction mixture is heated to boiling and kept boiling for 0.5 hours. Subsequently, the heating is stopped and 30 ml of acetone are stepwise added to the reaction mass, the mass being maintained for 3 hours at 10-15° C. The resulting crystalline residue is separated by filtrating, and is washed on the filter with acetone, and dried in vacuum. 5.6 g (88.5% from the theory) of the salt are obtained. The melting temperature is 128-129° C.

Obtained, %: C, 56.5, H 6.9. Calculated, %: C, 56.5, H 6.7.

NMR-$^1$H (DMSO-$d_6$): 2.12 (3H, s, $CH_3$), 2.26 (3H, s, $CH_3$), 2.31 (3H, s, $CH_3$), 2.42 (4H, s, $CH_2$), 6.79 (1H, s, CH-Py), 10.57 (b. s, COOH).

D). Preparation of 2,4,6-trimethyl-3-oxypyridine malate (Id)

0.8 g (0.00583 mol) of 2,4,6-trimethyl-3-oxypyridine base, 0.782 g (0.00583 mol) of hydroxy-butanedioic acid and 10 ml of methanol are fed to a flask with a magnetic stirrer and reflux condenser. Under stirring the reaction mixture is heated to boiling and kept boiling for 0.5 hours. Subsequently, the solvent is removed in vacuum. The oily residue is twice washed with acetone under stirring, and the solvent is removed by decantation. The resulting mass is vacuumed and maintained for one hour at residual pressure of 0.5 mm Hg. Subsequently, the mass is maintained for crystallization for 48-72 hours. A white solid compound with a melting temperature of 70-75° C. is obtained.

The yield is 1.12 g (70.8% from the theory). Obtained, %: C, 53.5, H 6.4. Calculated, %: 53.1. H 6.3.

NMR-$^1$H Bruker WM-400 (400 MHz) (DMSO-$d_6$): 2,12 (3H, s, $CH_3$); 2,26 (3H, s, $CH_3$); 2,30 (3H, s, $CH_3$); 3,11 (2H, s, $CH_2$); 2,41 (1H, doublet dubl. $J^2_{HAHB}$=15,7 Hz; $J^3_{HACH}$=5,4 Hz $CH_AH_B$); 4,2 ppm (1H, doublet dubl. $J^3_{CHHA}$=5,4 Hz; $J^3_{CHHB}$=7,4 Hz, CH).

EXAMPLE 2

Geroprotective Action of Compound 1 by the Example of Inhibition of Photoinduced Human Lipofuscin Granules of Liposome Peroxidation Liposomes are prepared from methanolic solution of cardiolipin (initial concentration: 5 mg/ml) by evaporation of methanol and solubilization of cardiolipin in a phosphate buffer. A mixture comprising a suspension of liposomes and lipofuscin granules, isolated from tissue of a retinal pigmentary epithelium of a human eye, is subjected to irradiation with intensive blue light under constant stirring. Concentration of lipid peroxidation products (TBK-active products) is determined after 20, 40, 60 and 90 minutes. The experimental sample contained 2 mM of a solution of compound Ic, or 2 mM of a solution of mexydole. The results of the experiment are listed in table 1.

TABLE 1

Inhibiting effect of compound Ic (in comparison to mexydole) regarding lipofuscin induced cardiolipin photoperoxidation

| Radiation time, min | Concentration of TBK-active products, nmol/mg lipid | | | Inhibition, % | |
|---|---|---|---|---|---|
| | Control | Compound Ic | Mexydole | Compound Ic | Mexydole |
| 0 | 1.83 | 1.83 | 1.83 | 0 | 0 |
| 20 | 3.0 | 2.42 | 2.84 | 20 | 5 |
| 40 | 3.5 | 2.53 | 3.5 | 28 | 0 |
| 60 | 4.52 | 2.85 | 4.5 | 40 | 0 |
| 90 | 5.38 | 3.28 | 5.0 | 40 | 7 |

The results indicate a protective effect of compound 1 regarding phototoxic action of the senile pigment-lipofuscin granules of the human eye. Under these conditions Mexydole practically did not show an inhibiting effect.

EXAMPLE 3

Antioxidant Action of Compound Ic with Respect to Ascorbate Induced Peroxidation of Photoreceptor Cells of a Pig's Eye The external segments of photoreceptor cells are obtained from pig retinas according to standard procedure, using methods of differential centrifuging in a saccharose density gradient. A mixture comprising a sodium-phosphate buffer (pH 7.3), $10^8$ segments/ml of external segments of photoreceptor cells, 0.5 mM ascorbic acid and 17 mM of compound Ic, was incubated in darkness under constant stirring for 15 and 30 minutes. Subsequently, the process was stopped by 15% trichloroacetic acid, and the concentration of TBK-active products has been determined. Samples being free of compound Ic were used as a control. The obtained results are shown in table 2a.

TABLE 2a

Inhibiting effect of compound Ic with respect to ascorbate-induced peroxidation of external segments of photoreceptor cells.

| Response time, min | Concentration of TBK-active products, relative units | | Inhibition, % |
|---|---|---|---|
| | Control | Compound IB | |
| 0 | 1 | 1 | — |
| 15 | 4.37 | 2.70 | 49.6 |
| 30 | 7.04 | 5.09 | 32.3 |

The comparison of antioxidant activity of compounds Ia, Ib, Ic and Id is shown in table 2b. In these experiments a comparison of the speed of ascorbate-induced peroxidation of external segments of photoreceptor cells of pig eyes has been carried out, said comparison being determined with respect to the accumulation of TBK-active products in the presence of different compound I salts.

TABLE 2b

Comparison of an inhibiting effect of compounds Ia,
b, c, d with respect to ascorbate-induced peroxidation
of external segments of photoreceptor cells.

| Compound I, concentration, mM | Speed of accumulation of TBK-active products for 30 min of reacting, nmol/mg | Inhibition, % |
|---|---|---|
| Control, 0 mM | 0.77 | — |
| Compound Ia, 44 mM | 0 | 100 |
| Compound Ib, 44 mM | 0.23 | 70 |
| Compound Ic, 43 mM | 0.05 | 93.5 |
| Compound Id, 43 mM | 0.1 | 87 |

The results indicate that all compound I salts show pronounced antioxidant activity regarding dark peroxidation of photoreceptor eye cells.

EXAMPLE 4

Determination of Antiradical Activity of Compound Ic in Comparison with Mexydole The efficiency of 3-hydroxypyridine derivatives as inhibitors of free radical reactions was determined by hemiluminescent method by means of measurement of speed constants of their reaction with ethyl-benzene $k_7$ peroxide radicals.

The measurements of intensity of chemiluminescence (HL) have been carried out with an apparatus CNK-7, designed and made by IHF RAN USSR. A photomultiplier FAU-38 is used as an optical receiver. The fixed concentration of radicals during oxidation of isopropyl toluene (cumole) is controlled by an initiator being azo-bis-isobutyronitrile.

In order to increase HL emission the activator chelate Eu (europium tristenoyl triphtoroacetonate with 1,10-phenatroline) has been used that has allowed to conduct measurements at low speed values of radical initiation ($W_1 = 10^{-8} - 10^{-9}$ mol/l.s.) and, therefore, at small amounts of added sample. A weighed amount of samples studied was diluted in an suitable solvent (chlorobenzene or acetonitrile) and a small amount of the prepared solution (0.1-0.25 ml) was added to the reaction mixture (5-6 ml), arranged in a temperature-controlled reaction vessel of the HL-device. The change of emission intensity was recorded. The obtained results are shown in table 3.

TABLE 3

Antiradical activity of p-oxyderivatives of nitrogen heterocycles
with respect to ethyl-benzene peroxide radicals.

| Compound | $k_7 \times 10^{-4}$ l/mol × sec |
|---|---|
| Metoxydole | 4.5 |
| Compound Ic | 9.5 |

The comparative evaluation of antiradical activity of compound 1 and mexydole has shown, that compound 1 shows a two times higher antiradical activity.

EXAMPLE 5

Study of the Influence of Compound Ic on Sizes of Necrosis Ischemia Zones in Case of an Acute Myocardial Ischemia The experiments are carried out with non-pedigree male rats having a weight of 250-300 g, which have been anesthetized with sodium ethaminale (40 mg/kg intraperitoneally). A myocardial infarction was modeled for animals, transferred to controlled breathing, by ligation of a descending branch of the left-hand coronary artery to a level of the lower edge of an auricula atrii.

The sizes of necrosis zones and ischemia zones have been determined within 4 hours after occlusion of the coronary artery by a differential indicator method, the principle of which is based on separate quantitative determination of Evans' blue (indicator of an ischemia zone) and red phormazane (indicator of an necrosis zone).

TABLE 4

Anti-ischemic activity of compound Ic in comparison
with other 3-oxypyridin derivatives (within 4 hours
after occlusion of the coronary artery of rats).

| Experimental conditions | Dose, mg/kg | Number of animals | Ratio of necrosis zone to total mass of the myocardium (%) | Ratio of necrosis zone to ischemia zone (%) |
|---|---|---|---|---|
| Control | — | 17 | 22 ± 2.0 | 68 ± 4.3 |
| Compound 1 | 16 | 7 | 4 ± 2.3 | 11 ± 3.3 |
| Emoxypine | 26 | 8 | 9 ± 2.4 | 32 ± 4.6 |
| Mexydole | 26 | 8 | 8 ± 1.4 | 46 ± 5.6 |
| Nicorandile | 12 | 8 | 10 ± 1.6 | 42 ± 5.4 |

As can be seen, compound Ic shows a considerably higher anti-ischemic activity than the other 3-oxypyridines.

EXAMPLE 6

Study of Local Irritant Action of Compound Ic to Tissue of the Eye

The experimental measurements are carried out on six rabbits. All animals have been subjected to single instillation of 1% solution of compound 1 into the right eye and 1% solution of emoxypine into the left eye. The front section of the eye is controlled by a focal illumination method with a 20 D lens within 1 min. after dropping. The results show, that:

A reaction of the conjunctiva of the eyelids and of the eyeglobes, or the cornea is not detected in the right eyes of the animals;

A pronounced conjunctival injection of the eyeglobe and a hyperemia of the conjunctiva of the low eyelid are observed in the left eyes of 4 animals. The other two animals show a moderate conjunctival injection of the eye.

The results, thus, demonstrate, that claimed compound Ic and the salts thereof have antioxidant, geroprotective and anti-ischemic activities and do not show local irritating action on tissue of the eye.

The comparative evaluation of antioxidant, antiradical geroprotective and anti-ischemic properties of compound Ic and drugs, widely used in medical practice being mexydole and emoxypine indicates a substantially higher efficiency and a lower toxicity of the claimed agent, and also indicates the prospectivity of the use of said agent in ophthalmic and cardiologic practice and other fields of medicine.

What is claimed is:

1. A method for preparing a pharmaceutically acceptable salt of 2,4,6-trimethyl-3-hydroxypyridine with a lower dicarboxylic acid, of formula (I)

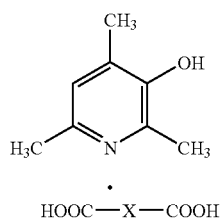

wherein

X is selected from the group consisting of a single bond, —CH$_2$—, —CH$_2$CH$_2$—, and —CH$_2$CH(OH)—said salt having antioxidant, geroprotective and anti-ischemic activity, said method comprising:

reacting equimolar amounts of 2, 4, 6-trimethyl-3-hydroxypyridine and a dicarboxylic acid in a solution of a lower alcohol at boiling temperature, treating the resulting reaction mixture with an organic solvent; and, optionally, maintaining the reaction mixture for 2-5 h at 10-15° C.

* * * * *